United States Patent [19]

Wiezer et al.

[11] Patent Number: 4,496,726

[45] Date of Patent: Jan. 29, 1985

[54] POLYTRIAZINYL ALCOHOLS, ESTERS AND URETHANES, A PROCESS FOR THEIR PREPARATION

[76] Inventors: Hartmut Wiezer; Gerhard Pfahler, both of Hoechst Aktiengesellschaft, D-6230, Frankfurt am Main 80, Fed. Rep. of Germany

[21] Appl. No.: 404,500

[22] Filed: Aug. 2, 1982

[30] Foreign Application Priority Data

Aug. 11, 1981 [DE] Fed. Rep. of Germany ....... 3131684

[51] Int. Cl.³ ............................................. C07D 401/12
[52] U.S. Cl. .................................... 544/198; 544/113; 544/212; 544/207; 544/209; 544/195; 524/100; 524/101; 528/423; 260/243.3
[58] Field of Search ............... 544/212, 113, 207, 209, 544/198, 195; 260/243.3; 528/423; 524/100

[56] References Cited

U.S. PATENT DOCUMENTS

| | | | |
|---|---|---|---|
| 4,234,728 | 11/1980 | Rody et al. | 544/198 |
| 4,288,593 | 9/1981 | Rody | 544/198 |
| 4,315,859 | 2/1982 | Nikles et al. | 544/207 |
| 4,335,242 | 6/1982 | Wiezer et al. | 544/198 |

FOREIGN PATENT DOCUMENTS 0002754 7/1979 European Pat. Off. .
0014683 8/1980 European Pat. Off. .
0029522 6/1981 European Pat. Off. .

Primary Examiner—John M. Ford
Attorney, Agent, or Firm—Connolly and Hutz

[57] ABSTRACT

Hitherto unknown polyalkylpiperidinylaminotriazines having a structure of the type

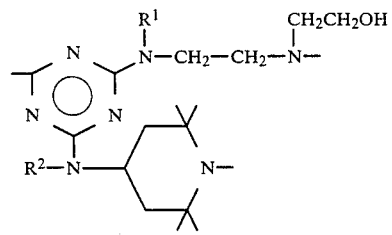

are obtained from halogenotriazinyl compounds and aminoethylaminoethanols and can be converted into further derivatives with isocyanates, esters and acid chlorides to give new stabilizers for polymers, which stabilizers are distinguished by very good migration resistance.

3 Claims, No Drawings

POLYTRIAZINYL ALCOHOLS, ESTERS AND URETHANES, A PROCESS FOR THEIR PREPARATION

Numerous polyalkylpiperidinylaminotriazines are known from the literature and have been suggested as stabilizers for polymers, but all of these also suffer from certain defects. Thus the products of German Offenlegungsschrift No. 2,636,144 are not satisfactory, in particular in respect of migration into fats, which manifests itself, for example, in their good solubility in heptane, while the compounds of European Pat. No. 14,683 contain considerable quantities of low-molecular constituents, which also increase the solubility in heptane. European Pat. No. 13,665 describes crosslinked products which are inadequate in respect of activity, and, finally, German Offenlegungsschrift No. 3,111,209 discloses high-molecular triazinyl esters and urethanes in which either the ester or the urethane group forms part of the polymer chain, or in which the monoalcohols used as educts carry only one triazinyl radical. These products are assessed as very good from the point of view of use technology, but, in spite of this, still cannot be regarded as optimal as far as their resistance to migration is concerned.

The aim of the present invention was, therefore, to obtain triazine derivatives which have a high molecular weight and which are favorably distinguished from the known stabilizers, particularly in respect of solubility in heptane, which is an indication of migration into fats.

It has been found that this requirement is substantially met by products containing further polar groups in addition to the polyalkylpiperidylamino groups.

The new compounds correspond to the general formula (I)

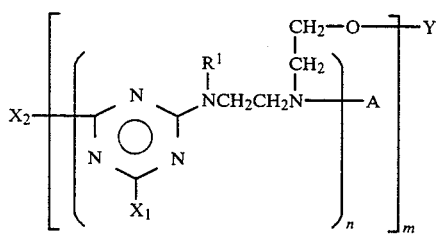

in which n is an integer from 1 to 100, preferably 1 to 20, in particular 1 to 10 and very particularly preferably 1, and m should be an integer from 1 to 20, preferably 1 to 4, but should, in particular, be 1 if n>1 and should, in particular, be >1 if n=1. $X_1$ represents halogen, preferably chlorine, phenyl or a group of the formula (II), (III) or (IV), preferably (II) or (III) and, in particular (II).

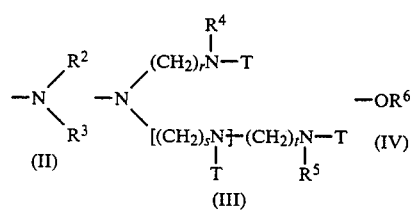

In formula (II), $R^2$ denotes hydrogen, $C_1$- to $C_{18}$-alkyl, $C_5$- to $C_{12}$-cycloalkyl which can be substituted by a $C_1$- to $C_4$-alkyl group, $C_3$- to $C_{12}$-alkenyl, phenyl which can be monosubstituted or disubstituted by Cl or $C_1$- to $C_4$-alkyl or by $C_1$- to $C_4$-alkoxy or by $C_1$- to $C_2$-carbalkoxy, or $C_7$- to $C_{14}$-phenylalkyl, preferably $C_7$- to $C_9$-phenylalkyl, or a group of the formula (V)

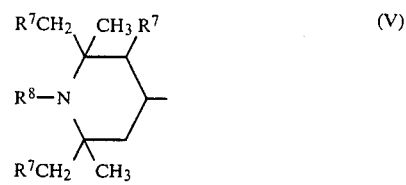

in which $R^7$=hydrogen or methyl, preferably hydrogen, and $R^8$=hydrogen, $C_1$- to $C_4$-alkyl which can be substituted by one OH group or, in the case of $C_3$-alkyl, can also be substituted by two OH groups, 2,3-epoxypropyl, allyl or benzyl, but preferably hydrogen.

$R^3$ is identical with or different from $R^2$ and has the meanings indicated under $R^2$ and additionally denotes $C_3$- to $C_{21}$-alkoxyalkyl, preferably $C_1$- to $C_{18}$-alkoxypropyl, in particular $C_1$- to $C_2$-alkoxypropyl, or denotes dimethylamino-$C_2$- to $C_5$-alkyl or diethylamino-$C_2$- to $C_5$-alkyl or denotes $C_2$- to $C_{18}$-hydroxyalkyl, preferably $C_2$- to $C_6$-hydroxyalkyl.

Together with the N atom linking them, $R^2$ and $R^3$ can also represent a pyrrolidine ring or a piperidine, morpholine or hexamethyleneimine ring which is unsubstituted or substituted by up to four $C_1$- to $C_4$-alkyl groups, preferably methyl groups.

In formula (III), the indices r, s and t denote identical or different integers from 2 to 6, preferably 2 or 3, v denotes an integer from 0 to 3, preferably 0 or 1 and especially 0, and $R^4$ and $R^5$ denote identical or different radicals having the meanings indicated under $R^2$, preferably hydrogen or a group of the formula (V), particularly hydrogen.

T denotes a group of the formula (VI)

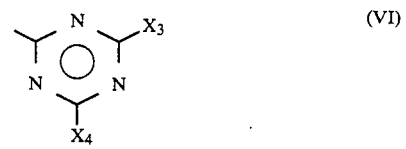

in which $X_3$ and $X_4$ are identical or different radicals of the formula (II), (III) or (IV), preferably (II) or (III) and especially (II).

In formula (IV), $R^6$ represents the radicals listed under $R^2$. In formula (I), $R^1$ denotes one of the radicals listed under $R^2$, preferably hydrogen, $C_1$- to $C_8$-alkyl, $C_5$- to $C_{12}$-cycloalkyl or the group of the formula (V), but particularly hydrogen, or the group of the formula (V).

If n=1, m is preferably an integer from 1 to 4 and $X_2$ represents one of the groups listed under $X_1$ and A then denotes a group of the formula (VI) in which $X_3$ is in this case preferably the same as $X_2$ having the meanings indicated above, and $X_3$ is preferably the same as $X_1$.

Y represents hydrogen or, depending on the meaning of m, represents an aliphatic, araliphatic, alicyclic, aromatic or heterocyclic monoacyl to polyacyl radical, monosulfonyl radical or monocarbamoyl to polycarbamoyl radical in which

having 1 to 40 C atoms is attached to —O— in formula (I) or Y represents

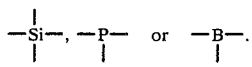

If m=1, Y is preferably hydrogen, a $C_1$- to $C_{18}$-aliphatic acyl group which can be substituted by —OH or —Cl, a $C_5$- to $C_{12}$-, preferably $C_6$-, alicyclic acyl radical which can be substituted by —OH or $C_1$- to $C_4$-alkyl, a $C_6$- or $C_{10}$-aromatic acyl or sulfonyl radical which can be substituted by —OH, $C_1$- to $C_4$-alkoxy, halogen, preferably chlorine, or —$NH_2$, a $C_7$- to $C_{16}$-, preferably $C_8$-, araliphatic acyl radical which can be substituted by —OH and/or 1 or 2 $C_1$- to $C_4$-alkyl groups, or a $C_1$- to $C_{18}$-alkyl group, a $C_5$- to $C_{12}$-, preferably $C_6$-, cycloalkyl group or a phenylcarbamoyl or naphthylcarbamoyl group which can be substituted by halogen, preferably —Cl, or by $C_1$- to $C_4$-alkyl.

If m=2, Y preferably denotes a $C_2$- to $C_{18}$-, preferably $C_3$- to $C_{10}$-, aliphatic radical which can be substituted by up to two OH groups, a $C_3$- to $C_{12}$-, preferably $C_5$- to $C_{12}$-, alicyclic radical which can be substituted by $C_1$- to $C_4$-alkyl, a phenyl, naphthyl or $C_7$- to $C_{16}$-araliphatic diacyl radical which can be substituted by —Cl or $C_1$- to $C_4$-alkyl, or a $C_2$- to $C_{12}$-, preferably $C_2$- to $C_6$-, and, in particular, $C_6$-, aliphatic $\alpha,\omega$-dicarbamoyl group, or a phenylenedicarbamoyl group which can be substituted by $C_1$- to $C_4$-alkyl or chlorine, or a $C_7$- to $C_{18}$-araliphatic dicarbamoyl group which can be substituted by up to four $C_1$- to $C_4$-alkyl groups.

If m=3, Y preferably represents a $C_2$- to $C_5$-aliphatic or $C_6$-aromatic triacyl radical which can be substituted by up to two OH groups, or represents groups of the formulae

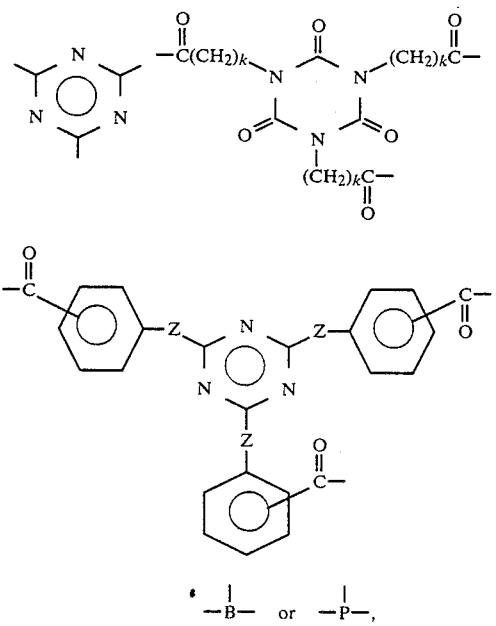

in which k is an integer from 1 to 6, preferably 1, and Z denotes —O— or

If m=4, Y is preferably a $C_4$- to $C_6$-aliphatic tetraacyl radical or a $C_6$- to $C_{10}$-aromatic tetraacyl radical or the group

If m=5 or 6, Y preferably represents a $C_5$- to $C_8$-aliphatic or cycloaliphatic radical or, if m>3, represents an oligomeric acyl radical which is derived from acrylic acid or derivatives thereof.

If n>1 and m=1, $X_2$ as a terminal group is halogen, preferably chlorine, or a radical of the formulae

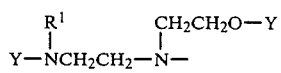

or

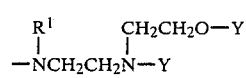

in which $R^1$ and Y have the meanings indicated above, and A as a terminal group is H or Y having the meanings indicated above.

At least one radical of the formula (V) must be present in formula (I), preferably, however, at least one radical of the formula (V) per monomer unit.

The new compounds are obtained in accordance with the following scheme of reactions, starting from a cyanuric halide, preferably cyanuric chloride.

With the exception of the reactions $A_4$ and $B_2$, the reactions can be carried out in any desired sequence; however, the sequence shown in the diagram represents the preferred procedure. In the formulae of the scheme of reactions, Hal, m, n, $R^1$, $X_1$, $X_2$ and Y have the meanings indicated above. In the case of reactants of the formulae H-$X_1$ and H-$X_2$, $X_1$ cannot be phenyl or halogen.

The individual process stages can be carried out with isolation of the intermediate products or can be accomplished without isolating the latter in a "one-pot variant".

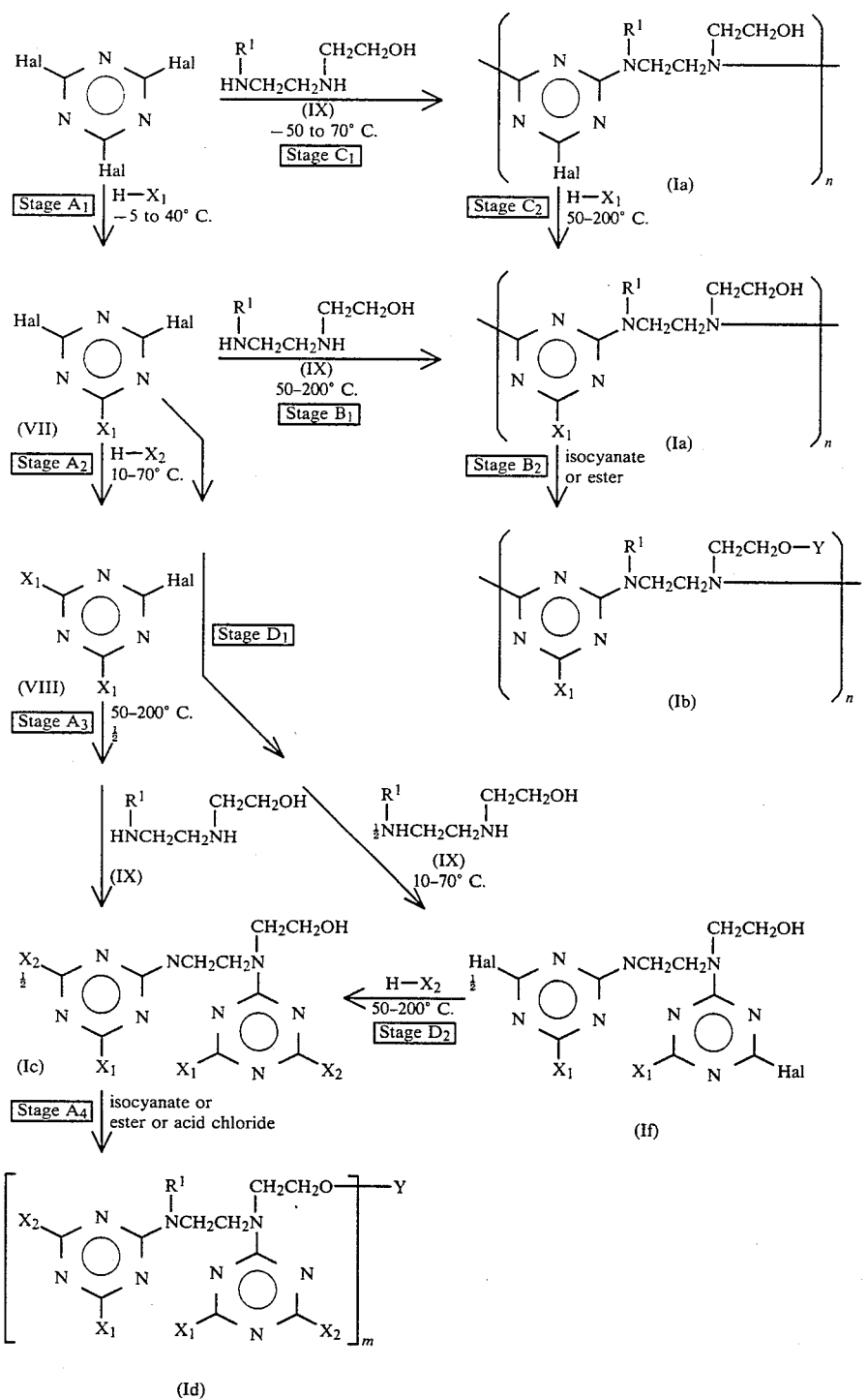

Specifically, the following procedure is used:

In process stage $A_1$, a cyanuric halide is reacted with a 0.95 to 1.05 molar, preferably a 1.0 molar, quantity of a compound of the formula $H-X_1$, resulting in the compounds (VII), which are reacted in process stage $A_2$ also with a 0.95 to 1.05 molar, preferably a 1.0 molar, quantity of a compound of the formula $H-X_2$, whereupon products of the formula (VIII) are formed. These compounds are subjected in process stage $A_3$ to a condensation reaction with 0.45 to 0.55 molar, preferably a 0.5 molar, quantity of a compound of the formula (IX)

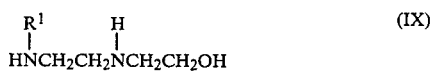

in which $R^1$ has the meanings indicated above, to give triazines, according to the invention, of the type (Ic). The latter can also be obtained by changing the order of the process stages $A_2/A_3$, ie. via $D_1/D_2$, by reacting the compounds (VII) with a 0.45 to 0.55 molar, preferably a 0.5 molar, quantity of a compound of the formula (IX) and subjecting the products thus prepared (If) to a condensation reaction with a 1.9 to 2.1 molar, preferably a 2.0 molar, quantity of $H\text{-}X_2$.

In process stage $B_1$, the products (VII) react with a 0.95 to 1.05 molar, preferably a 1.0 molar, quantity of a compound of the formula (IX) to give the triazines (Ia) according to the invention, which can, however, also be obtained via process stages $C_1$ and $C_2$ by reacting a cyanuric halide with a 0.95 to 1.05 molar, preferably a 1.0 molar, quantity of the compound (IX) and subjecting the product (Ie) thus obtained to a condensation reaction with a 0.95 to 1.05 equivalent, preferably a 1.0 equivalent, quantity of a compound of the formula $H\text{-}X_1$.

The compounds of the formula (Ib) or (Id) are obtained, if desired, via the process stages $B_2$ or $A_4$, respectively, from the compounds, according to the invention, (Ia) or (Ic), respectively, which are already good stabilizers, by reacting the latter with an equivalent quantity, relative to OH groups, of an isocyanate, ester or acid chloride.

The reactions are carried out in inert organic solvents, such as, for example, acetone, benzene, toluene, xylene, mesitylene or mixtures thereof.

Process stage $A_1$ is carried out at $-5°$ to $40°$ C., preferably $-5°$ to $20°$ C. and, in particular, $0°$ to $10°$ C., and process stage $C_1$ is carried out at $-5$ to $70$, preferably $-5°$ to $20°$ C., for the replacement of the first halogen atom and at $30°$ to $70°$ C. for the replacement of the second halogen atom, in particular at $0°$ to $10°$ C. for the replacement of the first halogen atom and at $40°$ to $70°$ C. for the replacement of the second halogen atom.

Process stages $A_2$ and $D_1$ require a reaction temperature of 10 to 70, preferably 30 to 70 and, in particular, $40°$ to $70°$ C. Process stages $B_1$, $A_3$, $C_2$ and $D_2$ are carried out at 50 to 200, preferably 80 to 180, and, in particular, $100°$ to $180°$ C.

The reactions in accordance with process stage $A_4$ and $B_2$ require temperatures of 90 to 180, preferably 100 to 180 and, particularly in the case of transesterification reactions, $130°$ to $180°$ C.

In stages $B_1$, $A_1$, $A_2$, $A_3$, $C_1$, $C_2$, $D_1$ and $D_2$, equivalent quantities of inorganic bases are added as hydrogen halide acceptors when preparing the new compounds. Examples of suitable inorganic bases are sodium hydroxide, potassium hydroxide, sodium carbonate and potassium carbonate, in a solid form or in aqueous solution.

If it is desired to react isocyanates with (Ia) or (Ic) in accordance with $B_2$ or $A_4$, the reaction is catalyzed by 0.1 to 2% by weight, relative to (Ia) or (Ic), respectively, of a base, such as, for example, 1,4-diazabicyclo-[2.2.2]-octane or KOH. The transesterification reactions require strong bases such as, for example, NaH, LiNH$_2$ or alkali metal alcoholates, as catalysts. For the reaction with acid chlorides, the triazines (Ic) are previously converted by known processes into their alkali metal alcoholates.

The following are examples of starting substances of the formulae $H\text{-}X_1$ and $H\text{-}X_2$ according to the reaction diagram, which are identical with the radicals of the formulae (II), (III) and (IV) when the latter are saturated in respect of H:
(1) ammonia
(2) methylamine
(3) butylamine
(4) hexylamine
(5) dodecylamine
(6) 2-ethyl-hexylamine
(7) octadecylamine
(8) cyclohexylamine
(9) benzylamine
(10) 3-methoxypropylamine
(11) 3-octadecyloxypropylamine
(12) 3-dimethylaminopropylamine
(13) diethylamine
(14) dibutylamine
(15) dicyclohexylamine
(16) dioctadecylamine
(17) piperidine
(18) morpholine
(19) 2-aminoethanol
(20) 3-aminopropanol
(21) methanol
(22) ethanol
(23) 2,2,6,6-tetramethyl-4-amino-piperidine
(24) 2,2,6,6-tetramethyl-4-butylamino-piperidine
(25) 2,2,6,6-tetramethyl-4-octadecylamino-piperidine
(26) 2,2,6,6-tetramethyl-4-(3-methoxy)-propylamino-piperidine
(27) 2,2,6,6-tetramethyl-4-(3-dimethylamino)-propylamino-piperidine
(28) N-(2,2,6,6-tetramethyl-4-piperidyl)-3-ethoxy-propylamine
(29) 2,2,6,6-tetramethyl-4-piperidylamino-propan-3-ol
(30) N-(2,2,6,6-tetramethyl-4-piperidyl)-cyclododecylamine
(31) N-(2,2,6,6-tetramethyl-4-piperidyl)-hexylamine
(32) 2,2,6,6-tetramethylpiperidin-4-ol
(33) di-(2,2,6,6-tetramethyl-4-piperidinyl)-amine
(34) 1,9-bis-[2,4-bis-<N-(2,2,6,6-tetramethyl-4-piperidinyl)-3-methoxypropylamino>-1,3,5-triazin-6-yl]-1,5,9-triazanonane
(35) 1,7-bis-[2,4-bis-<N-(2,2,6,6-tetramethyl-4-piperidinyl)-3-methoxypropylamino>-1,3,5-triazin-6-yl]-1,4,7-triazaheptane
(36) 1,5,12-tris-[2,4-bis-<N-(2,2,6,6-tetramethyl-4-piperidinyl)-3-methoxypropylamino>-1,3,5-triazin-6-yl]-1,5,8,12-tetraazadodecane The following are examples of compounds of the formula

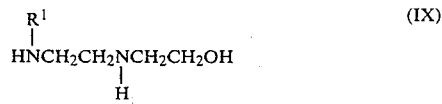

(37) N-[(2-aminoethyl)-amino]-ethanol
(38) N-{[2-<N-(2,2,6,6-tetramethyl-4-piperidinyl)>-aminoethyl]-amino}-ethanol
(39) N-[<2-(N'-butyl)-aminoethyl>-amino]-ethanol
(40) N-[<2-(N'-cyclohexyl)-aminoethyl>-amino]-ethanol The following are examples of isocyanates, esters and acid chlorides which can be reacted with compounds of the formulae (Ia) or (Ic):
(41) methyl isocyanate
(42) butyl isocyanate
(43) octadecyl isocyanate
(44) cyclohexyl isocyanate
(45) hexamethylene diisocyanate
(46) tolylene-2,4-diisocyanate

(47) polyurethanes containing free isocyanate terminal groups
(48) methyl caprylate
(49) methyl butyrate
(50) ethyl acetate
(51) methyl methacrylate
(52) diethyl malonate
(53) dimethyl succinate
(54) dimethyl adipate
(55) dimethyl suberate
(56) dimethyl sebacate
(57) dimethyl dodecanedioate
(58) dimethyl terephthalate
(59) dimethyl maleate
(60) dimethyl fumarate
(61) dimethyl itaconate
(62) dimethyl malate
(63) trimethyl 1,2,4-benzenetricarboxylate
(64) tetramethyl 1,2,3,5-benzenetetracarboxylate
(65) dimethyl tetrahydrophthalate
(66) diethyl bis-carboethoxymethylenemalonate
(67) 1,3,5-tris-(carboethoxymethylene) isocyanurate
(68) 1,3,5-tris-(carbomethoxymethylene) isocyanurate
(69) 1,3,5-tris-(carbomethoxyethylene) isocyanurate
(70) tris-2,4,6-[4-(carboethoxy)-phenoxy]-1,3,5-triazine
(71) diethyl 2-carboethoxymethylene-malonate
(72) diethyl 2,2-bis-(carboethoxymethylene)-malonate
(73) sebacic acid dichloride
(74) adipic acid dichloride
(75) cyanuric chloride
(76) silicon tetrachloride
(77) boron trichloride
(78) phosphorus trichloride The new compounds are distinguished in many respects from the known triazinylamine stabilizers, both in their structure and also in their properties. Thus the oligomeric triazinylamines described in the patent literature (for example German Pat. No. 2,636,144, German Offenlegungsschriften Nos. 2,933,078 and 3,022,896; European Patent Application No. 13,665) are not substituted by hydroxyalkyl, ester or urethane groups at the diamino components which link the triazine structural units, while the high-molecular triazinyl compounds known from German Offenlegungsschrift No. 3,111,209 admittedly contain ester and/or urethane groups, but the latter form part of the polymer chain, or the monoalcohols used as educts contain only one triazinyl radical.

Compared with the group comprising the oligomeric triazinylamine stabilizers, the new products are distinguished, in particular, by their lower solubility in heptane, which suggests a low solubility in fats, ie. a high migration resistance. This was not to be expected and must be regarded as surprising.

Furthermore, particularly when compared with the products of the nearest state of the art, namely those of German Offenlegungsschrift No. 3,111,209, a lower volatility at a longer exposure to heat and improved effectiveness would not have been expected. On the contrary, because of the similar structure, a comparable suitability as stabilizers would have been expected. Finally, it is particularly surprising that even the members of the new products in which Y is H, have an excellent migration resistance to aqueous media, in spite of the large number of OH groups.

The new triazine stabilizers can be incorporated without problems into the polymers to be stabilized and are excellently suitable for stabilizing the latter against oxidative degradation induced by light. Further properties which should be singled out are compatibility even when non-polar plastics in spite of the polar character of the compounds, and also the properties already claimed of migration resistance against extraction by washing with water, sparing solubility in heptane with reference to migration into fats and low volatility in comparison with the stabilizers of German Offenlegungsschrift No. 3,111,209.

As mentioned several times, the new compounds are used as stabilizers for synthetic polymers against damage to the latter caused by the action of oxygen, heat and light. Examples of such plastics and stabilization examples are listed in German Offenlegungsschrift No. 3,113,455, pages 19 to 24, and in German Offenlegungsschrift No. 3,111,209, pages 23 to 28. Preferred polymers are polyolefins, polyacrylates and polymethacrylates and homopolymers and copolymers of styrene, particularly the first-mentioned.

In general, the stabilizer is employed in quantities of 0.01 to 5 parts by weight, relative to the polymer, if appropriate together with the previously known stabilizers and additives such as are described in German Offenlegungsschrift No. 3,111,209 on pages 26 to 28.

The examples which follow serve to illustrate the invention further.

In the preparation examples which follow, the starting materials employed, insofar as they are not mentioned by name, are characterized by numerals which relate to the numbering of the substances listed on pages 12 to 16. Since the process products are resins, the melting point data are "approximate" values.

EXAMPLE 1

N,N'-bis-[2,4-bis-<N-(2,2,6,6-Tetramethyl-4-piperidinyl)-3-methoxypropane-1-amino>-1,3,5-triazin-6-yl]-2-[(2-aminoethyl)-amino]-ethanol 226.8 g (0.4 mole) of 6-chloro-[2,4-bis-<N-(2,2,6,6-tetramethyl-4-piperidinyl)-3-methoxy-propane-1-amino>]-1,3,5-triazine, 21.2 g (0.2 mole) of 2-[(2-aminoethyl)amino]-ethanol (starting substance 37) and 16.4 g (0.4 mole) of NaOH powder in 800 ml of xylene were boiled under reflux for 20 hours in a 2 l stirred apparatus, the water of reaction being removed from the system in a water separator. NaCl was then filtered off and the filtrate was concentrated to dryness in vacuo. The residue was 220 g (94.3%) of a nearly colorless resin. Melting point 106° to 111° C.

EXAMPLE 2

N,N'-bis[2,4-bis-<N-(2,2,6,6-Tetramethyl-4-piperidinyl)butylamino>-1,3,5-triazin-6-yl]-2-[(2-aminoethyl)-amino]-ethanol This compound, melting point ~90° C., was obtained by the procedure of Example 1 from 6-chloro-[2,4-bis-<N-(2,2,6,6-tetramethyl-4-piperidinyl)-butylamino>]-1,3,5-triazine and compound No. 37.

EXAMPLE 3

N,N'-bis-[2-<N-(2,2,6,6-Tetramethyl-4-piperidinyl)-3-ethoxypropane-1-amino>-4-<dicyclohexylamino>-1,3,5-triazin-6-yl]-2-[(2-aminoethyl)-amino]-ethanol This was prepared analogously to Example 1 from 6-chloro-[2-<N-(2,2,6,6-tetramethyl-4-piperidinyl)-3-ethoxypropane-1-amino>]-4-<dicyclohexylamino>-

1,3,5-triazine and compound No. 37. Melting point ~95° C.

EXAMPLE 4

N,N'-bis-[2-<N-(2,2,6,6-Tetramethyl-4-piperidinyl)-3-methoxypropane-1-amino>-4-<dioctadecylamino>-1,3,5-triazin-6-yl]-2-[(2-aminoethyl)-amino]-ethanol This was prepared analogously to Example 1 from 6-chloro-[2-<N-(2,2,6,6-tetramethyl-4-piperidinyl)-3-methoxypropane-1-amino>]-4-<dioctadecylamino>-1,3,5-triazine and compound No. 37 and was obtained in the form of a viscous resin.

EXAMPLE 5

N,N'-bis-[2-chloro-4-<N-(2,2,6,6-tetramethyl-4-piperidinyl)-butylamino>-1,3,5-triazin-6-yl]-2-{[2-<N-(2,2,6,6-tetramethyl-4-piperidinyl)>-aminoethyl]-amino}-ethanol 92.2 g (0.5 mole) of cyanuric chloride, 500 ml of toluene and 250 ml of acetone were initially taken in a 2 l stirred apparatus. 106 g (0.5 mole) of compound No. 24 were first added dropwise at 0° to 10° C., and 80 g (0.5 mole) of 25% strength sodium hydroxide solution were then added dropwise in the course of 3 hours at 10° C. 62.0 g (0.25 mole) of compound No. 38 were then added, after which the mixture was heated to 60° C. and 80 g (0.5 mole) of 25% strength NaOH were added dropwise at 60° C. in the course of 2 hours. The mixture was stirred for a further 30 minutes and, after adding 150 ml of acetone and 100 ml of water, the organic phase was separated off. After drying over Na$_2$SO$_4$, it was filtered and the filtrate was concentrated to dryness in vacuo. 218.7 g=98.2% of theory of a solid, pale resin, melting point 115° C.

EXAMPLES 6 TO 9

The reaction was carried out as in Example 5 and the following were obtained:

EXAMPLE 6

N,N'-bis-[2-Chloro-4-<N-(2,2,6,6-tetramethyl-4-piperidinyl)-3-ethoxypropane-1-amino>-1,3,5-triazin-6-yl]-2-{[2-<N-(2,2,6,6-tetramethyl-4-piperidinyl)>-aminoethyl]-amino}-ethanol Melting point ~80° C., from cyanuric chloride, compound No. 28 and compound No. 38.

EXAMPLE 7

N,N'-bis-[2-Chloro-4<N-(2,2,6,6-tetramethyl-4-piperidinyl)-butylamino>-1,3,5-triazin-6-yl]-2-[(2-aminoethyl)-amino]-ethanol Melting point ~130° C., from cyanuric chloride, compound No. 24 and compound No. 37.

EXAMPLE 8

N,N'-bis-[2-Chloro-4-<N-(2,2,6,6-tetramethyl-4-piperidinyl)-3-ethoxypropane-1-amino>-1,3,5-triazin-6-yl]-2-[(2-aminoethyl)-amino]-ethanol Melting point ~100° C., from cyanuric chloride, compound No. 28 and compound No. 37.

EXAMPLE 9

N,N'-bis-[2-Chloro-4-<N-(2,2,6,6-tetramethyl-4-piperidinyl)-3-dimethylamino-propane-1-amino>-1,3,5-triazin-6-yl]-2-[(2-aminoethyl)-amino]-ethanol Melting point ~250° C., from cyanuric chloride, compound No. 27 and compound No. 37, in this example working-up being effected by concentrating the whole reaction solution to dryness in vacuo, taking up the residue in 2 l of warm ethanol, filtering off NaCl and concentrating the filtrate to dryness in vacuo.

EXAMPLE 10 (A POLYMERIC TRIAZINE)

26.0 g (0.069 mole) of 2,4-dichloro-6-<N-(2,2,6,6-tetramethyl-4-piperidinyl)-3-methoxypropane-1-amino>-1,3,5-triazine, 7.2 g (0.069 mole) of compound No. 37 and 5.5 g (0.138 mole) of NaOH powder in 100 ml of xylene were boiled under reflux for 24 hours in a 250 ml stirred apparatus. The mixture was then filtered while hot and the filtrate was concentrated to dryness in vacuo. The residue was a colorless, solid resin.

26.5 g=94.4% of theory; melting point ~125° C.

EXAMPLES 11 TO 14

The following products were prepared analogously:

| Example No. | Educt 1 Compound from Example | Educt 2 Compound No. | Melting point (°C.) of the process product |
| --- | --- | --- | --- |
| 11 | 7 | 37 | 169–91 |
| 12 | 8 | 37 | 183–92 |
| 13(+) | 5 | 38 | 145–90 |
| 14 | 9 | 37 | 94–105 |

(+)Reaction medium mesitylene at 160° C.

EXAMPLE 15

233.2 g (0.2 mole) of the compound obtained in Example 1 were initially taken together with 800 ml of toluene and 1 g of 1,4-diazabicyclo-[2.2.2]-octane in a 2 l stirred apparatus, 16.8 g (0.1 mole) of compound No. 45 were then added dropwise at 50° C. and the reaction mixture was stirred at reflux temperature for 20 hours. It was then concentrated to dryness in vacuo.

249 g of a resin, melting point 132° to 154° C.

EXAMPLE 16

The reaction was carried out as in Example 15, and reacting 12.6 g (0.03 OH equivalent) of the compound according to Example 12 with 3.8 g (0.03 mole) of compound No. 44 and 0.1 g of 1,4-diazabicyclo-[2.2.2]-octane as catalyst in 100 ml of toluene gave 15.7 g of a resin, melting point ~200° C.

EXAMPLE 17

18 g of a soft resin were obtained as described in Example 15 from 17.8 g (0.01 mole) of the compound according to Example 4, 0.85 g (0.005 mole) of compound No. 45 and 0.1 g of 1,4-diazabicyclo-[2.2.2]-octane in 100 ml of toluene.

EXAMPLE 18

22.0 g (0.02 mole) of the compound according to Example 3 and 1.6 g (0.01 mole) of compound No. 52 in 100 ml of anhydrous mesitylene were heated at 160° C. and approx. 0.3 g of LiNH$_2$ were added, whereupon 0.9 g of ethanol was removed by distillation in the course of approx. 10 hours. The solution was decolorized by means of fuller's earth and active charcoal and was concentrated to dryness in vacuo. 22 g of a yellowish resin were obtained. Melting point 78° to 90° C.

EXAMPLES 19 TO 23

The following compounds were prepared as indicated in Example 18:

| Example No. | Educt 1 Compound from Example | Educt 2 Compound No. | Melting point (°C.) of the process product |
|---|---|---|---|
| 19 | 1 | 53 | resin |
| 20 | 12 | 49 | 140 |
| 21 | 1 | 56 | 80 |
| 22 | 12 | 50 | 130 |
| 23 | 7 | 48 | resin |

EXAMPLE 24

Tetrakis-{N,N'-bis-[2,4-bis-<N-(2,2,6,6-tetramethyl-4-piperidinyl)-butylamino>-1,3,5-triazin-6-yl]-2-[(2-aminoethyl)-amino]-ethoxy{-silane 22.0 g (0.02 mole) of the compound according to Example 2 and 0.6 g (0.02 mole) of 80% strength NaH in 100 ml of anhydrous mesitylene were boiled under reflux until no further $H_2$ was formed. 0.85 g (0.005 mole) of $SiCl_4$, dissolved in 10 ml of mesitylene, was then added dropwise at 20° C. The temperature was raised to 120° C. and stirring was continued for 10 hours. The mixture was then filtered and the filtrate was concentrated to dryness in vacuo. 18 g of a pale resin, melting point 105° C.

EXAMPLE 25

The reaction was carried out analogously to Example 24, using 35.0 g (0.03 mole) of the compound according to Example 1, 0.03 mole of NaH and 1.84 g (0.01 mole) of cyanuric chloride.

35 g of a resin; melting point 130° C.

EXAMPLE 26

This example demonstrates the volatility of the new triazine stabilizers in comparison with a product of the nearest state of the art.

The volatility figures were determined in an apparatus for thermogravimetric analysis. Equal quantities (500 mg) of the compounds according to the invention and of the comparison substance were heated to 300° C. in a nitrogen atmosphere at a rate of heating of 2K/minute, and the loss of substance in mg/cm$^2$ of sample surface was measured. The results are shown in the following table:

| Stabilizer according to Example | Loss of weight in mg/cm$^2$ on reaching ... °C. | | | | |
|---|---|---|---|---|---|
| | 220 | 260 | 300 | 10 minutes at 300° C. | 30 minutes at 300° C. |
| Comparison[1] | 0.32 | 1.11 | 9.48 | 58.46 | 118.5 |
| Comparison[2] | 0.79 | 2.69 | 5.01 | 9.48 | 22.1 |
| 15 | 0.16 | 0.95 | 4.32 | 6.95 | 15.8 |
| 11 | 0.47 | 1.58 | 8.05 | 8.69 | 12.6 |
| 24 | 0.16 | 1.74 | 4.26 | 6.48 | 14.1 |
| 10 | 0.0 | 1.26 | 3.00 | 5.37 | 9.3 |

[1]Compound according to Example 1 of German Offenlegungsschrift 2,719,131
[2]Compound according to Example 2 of German Offenlegungsschrift 3,111,209

EXAMPLE 27

A mixture, prepared in a high-speed laboratory mixer, comprising: 100 parts by weight of polypropylene (®Hostalen PPU VP 1770 F made by Hoechst AG having a melt index MFI 190/5 of 1.9 g/10 minutes, determined as specified in DIN 53,535), 0.2 part by weight of calcium stearate, 0.1 part by weight of pentaerythrityl tetrakis-3-(3,5-di-tert.-butyl-4-hydroxyphenyl)-propionate and 0.3 part by weight of the stabilizer to be tested was processed to give granules. The material which had been stabilized in this manner was then melted in a laboratory extruder under the customary processing conditions and was spun into monofilaments via a spinning pump equipped with an eight-point spinning head. These monofilaments were then subsequently stretched in a ratio of 1:3 and were texturized to give yarn of 40 dtex, which was processed to give test fabrics.

The samples of fabric were mounted on a perforated piece of cardboard in such a way that a free aperture of approx. 15.5 mm diameter was left, and in this form were subjected to irradiation with alternating light in a Xeno-test X 1200 apparatus made by Original Hanau Quarzlampen GmbH. The intensity of radiation was modulated by a UV filter (special filter glass d=1.7 mm), and the test method specified in DIN 53,387 (a dry period of 17 minutes, sprinkling for 3 minutes, blackbody temperature 45° C. and relative atmospheric humidity during the dry period 70 to 75%) was used. At definite intervals of time the fabric was loaded centrally with a weight of 6 mm diameter and a pressure of 0.1N/mm$^2$. The point at which the weight broke through was taken as the time of failure.

| Stabilizer according to Example | Exposure time in hours |
|---|---|
| Polypropylene Comparison[3] | <280 |
| Comparison[1] | 1,400 |
| Comparison[2] | 3,100 |
| Comparison[3] | 400 |
| 15 | <3,100[4] |
| 13 | <3,100[4] |

[1]Compound according to Example 1 of German Offenlegungsschrift 2,719,131
[2]Compound according to Example 2 of German Offenlegungsschrift 3,111,209
[3]Without stabilizer
[4]Weight had not yet broken through

EXAMPLE 28

The stabilized granules prepared as in the preceding example were converted into blown film of approx. 70 μm thickness on a Laboratory film blowing unit (screw diameter 25 mm, length 20 D, temperature program 200°, 240°, 250° and 255° C.). Pieces of this film were artificially weathered in the Xenotest X 1200 apparatus as described in Example 27. The carbonyl number was determined, as a criterion of damage, by a method modelled on DIN 63,383, part 2 (for PP this is defined as the ratio of the extinction values at 1,715 cm$^{-1}$ and 1,524 cm$^{-1}$).

| Stabilizer according to Example | C = 0 number after ... hours | | | |
|---|---|---|---|---|
| | 500 | 1,000 | 2,000 | 2,500 |
| Polypropylene Comparison[1] | <2 | <2 | | |
| Comparison[2] | 0.1 | <0.1 | 0.4 | 0.9 |

| Stabilizer according to Example | C = 0 number after ... hours | | | |
| --- | --- | --- | --- | --- |
| | 500 | 1,000 | 2,000 | 2,500 |
| Comparison[3] | <2 | | | |
| 15 | <0.1 | <0.1 | 0.2 | 0.4 |
| 13 | <0.1 | <0.1 | 0.3 | 0.6 |

[1,2] and [3]correspond to the comparison samples of Example 27.

EXAMPLE 29

In order to determine the solubility, which constitutes a measure of the resistance to migration, 1 g portions of the stabilizer to be tested were stirred in 9 g of heptane at 25° C. for 10 minutes. The insoluble material was filtered off, dried and weighed.

| Stabilizer according to Example | Solubility, % at 25° C. |
| --- | --- |
| 11 | 0 |
| 12 | 0 |
| 13 | 10 |
| 14 | 0 |
| 15 | 10 |
| Comparison[1] | 100 |
| Comparison[2] | 80 |

[1]Stabilizer according to Example 6 of German Offenlegungsschrift 2,636,144
[2]Stabilizer according to Example 2 of German Offenlegungsschrift 3,111,209

We claim:

1. A polytriazinyl compound of the formula (I)

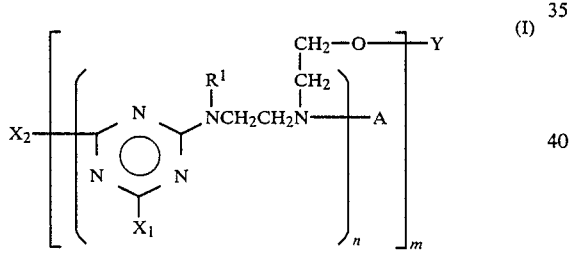

in which n is an integer from 1 to 100 and m is an integer from 1 to 20, $X_1$ represents halogen, phenyl or a group of the formula (II), (III) or (IV)

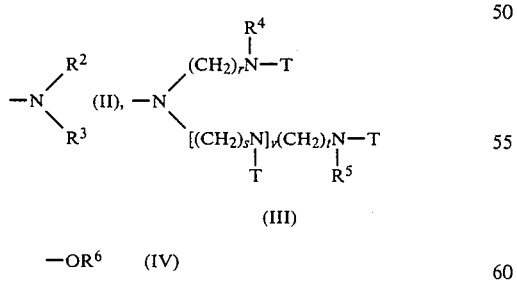

—$OR^6$ (IV)

in which formulae $R^2$ is hydrogen, $C_1$- to $C_{18}$-alkyl, $C_5$- to $C_{12}$-cycloalkyl which can be substituted by a $C_1$- to $C_4$-alkyl group, $C_3$- to $C_{12}$-alkenyl, or phenyl which can be substituted by one or two Cl atoms or by one or two $C_1$- to $C_4$-alkyl groups or by $C_1$- to $C_4$-alkoxy or $C_1$- to $C_2$-carboalkoxy, or $C_7$- to $C_{14}$-phenylalkyl or a group of the formula (V)

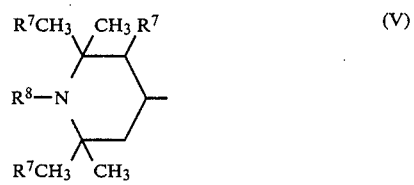

in which $R^7$=hydrogen or methyl and $R^8$=hydrogen, $C_1$- to $C_4$-alkyl which can be substituted by one OH group or, in the case of $C_3$-alkyl, can also be substituted by two OH groups, 2,3-epoxypropyl, allyl or benzyl; $R^3$ is identical with or different from $R^2$ and has the meanings indicated under $R^2$ and additionally represents $C_3$- to $C_{21}$-alkoxyalkyl or dimethylamino-$C_2$- to $C_5$-alkyl or diethylamino-$C_2$- to $C_5$-alkyl or, together with the N atom linking them, $R^2$ and $R^3$ represent a pyrrolidine ring or a piperidine, morpholine or hexamethyleneimine ring which is unsubstituted or substituted by up to four $C_1$- to $C_4$-alkyl groups; r, s and t represent identical or different integers from 2 to 6 and v represents an integer from 0 to 3; $R^4$ and $R^5$ are identical or different radicals having the meanings indicated under $R^2$ and T is a group of the formula (VI)

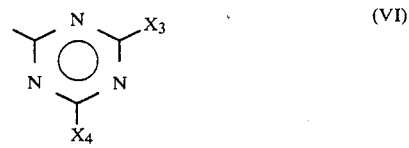

in which $X_3$ and $X_4$ are identical or different radicals of the formulae (II), (III) or (IV) and $R^6$ represents one of the radicals listed under $R^2$; $R^1$ has the meaning of one of the radicals listed under $R^2$; $X_2$ represents one of the groups indicated under $X_1$, A is a group of the formula (VI) and, if m=1, Y is a $C_1$- to $C_{18}$-aliphatic acyl group which can be substituted by —OH or —Cl, a $C_5$- to $C_{12}$-alicyclic acyl radical which can be substituted by —OH or $C_1$- to $C_4$-alkyl, a $C_6$- or $C_{10}$-aromatic acyl or sulfonyl radical which can be substituted by —OH, $C_1$- to $C_4$-alkoxy, halogen or —NH$_2$, a $C_7$- to $C_{16}$-araliphatic acyl radical which can be substituted by —OH and/or 1 or 2 $C_1$- to $C_4$-alkyl groups, or a $C_1$- to $C_{18}$-alkyl group, a $C_5$- to $C_{12}$-cycloalkyl group or a phenylcarbamoyl or naphthylcarbamoyl group which can be substituted by halogen or by $C_1$- to $C_4$-alkyl, if m=2, Y represents a $C_2$- to $C_{18}$-aliphatic radical which can be substituted by up to two OH groups, a $C_3$- to $C_{12}$-alicyclic radical which can be substituted by $C_1$- to $C_4$-alkyl, a phenyl, naphthyl or $C_7$- to $C_{16}$-araliphatic diacyl radical which can be substituted by —Cl or $C_1$- to $C_4$-alkyl, or a $C_2$- to $C_{12}$-aliphatic α,ω-dicarbamoyl group, or a phenylenedicarbamoyl group which can be substituted by $C_1$- to $C_4$-alkyl or chlorine, or a $C_7$- to $C_{18}$-araliphatic dicarbamoyl group which can be substituted by up to four $C_1$- to $C_4$-alkyl groups, if m=3, Y represents a $C_2$- to $C_5$-aliphatic or $C_6$-aromatic triacyl radical which can be substituted by up to two OH groups, or represents groups of the formulae

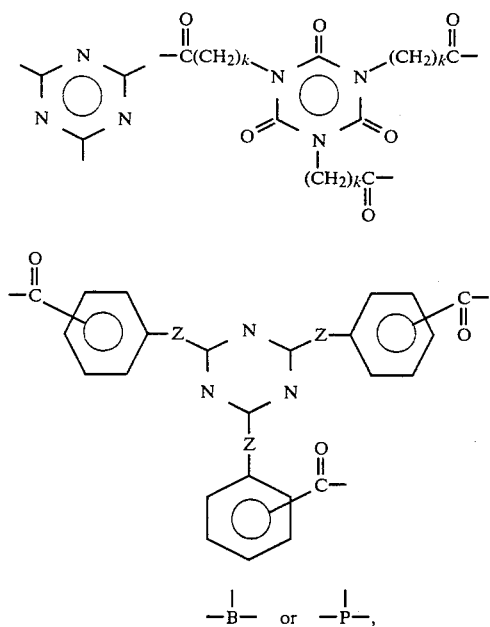

in which k is an integer from 1 to 6 and Z denotes —O— or

if m=4, Y is a $C_4$- to $C_6$-aliphatic tetraacyl radical or a $C_6$- to $C_{10}$-aromatic tetraacyl radical or the group

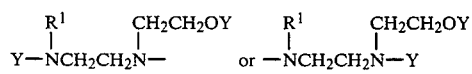

if m=5 or 6, Y represents a $C_5$- to $C_8$-aliphatic or cycloaliphatic radical or, if m>3, represents an oligomeric acyl radical which is derived from acrylic acid or derivatives thereof, if n>1 and m=1, $X_2$ as a terminal group is halogen or one of the radicals

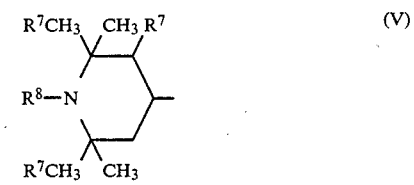

in which $R^1$ and Y have the meanings indicated above, A as a terminal group is H or Y, and at least one radical of the formula (V) must be present in formula (I).

2. A polytriazinyl compound of claim 1, wherein:
if m=1, and Y is a group substituted with halogen, said halogen is chlorine;
if m=2 and Y is an aliphatic radical, said aliphatic radical contains 3 to 10 carbon atoms, and, if said $C_3$- to $C_{10}$-aliphatic radical is substituted with an alicyclic radical, said alicyclic radical contains 5 to 12 carbon atoms, and said aliphatic alpha, omega-dicarbamoyl, if present, contains 2 to 6 carbon atoms; and if m=3, k is 1.

3. A process for the preparation of the polytriazinyl compounds of the formula (I)

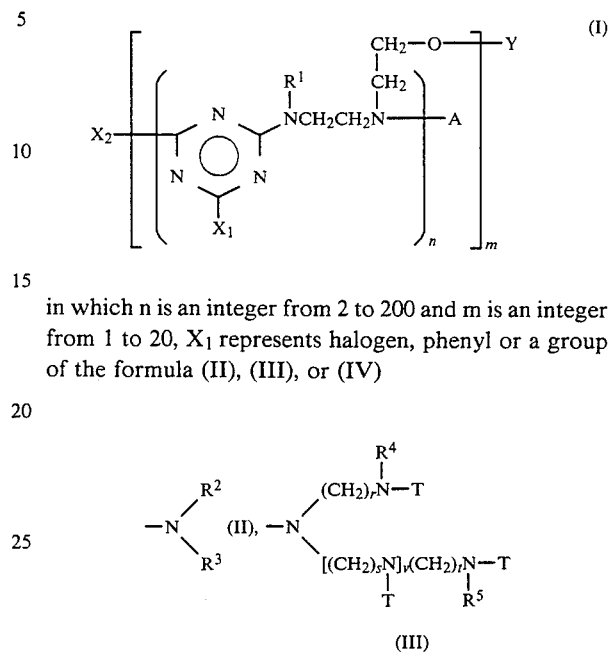

in which n is an integer from 2 to 200 and m is an integer from 1 to 20, $X_1$ represents halogen, phenyl or a group of the formula (II), (III), or (IV)

$$-N\begin{matrix}R^2\\R^3\end{matrix} \quad (II), \quad -N\begin{matrix}(CH_2)_rN-T\\ \\ [(CH_2)_sN]_v(CH_2)_rN-T\end{matrix}\begin{matrix}R^4\\ \\ \\ R^5\end{matrix}$$

(III)

$-OR^6$ (IV)

in which formulae $R^2$ is hydrogen, $C_1$- to $C_{18}$-alkyl, $C_5$- to $C_{12}$-cycloalkyl which can be substituted by a $C_1$- to $C_4$-alkyl group, $C_3$- to $C_{12}$-alkenyl, or phenyl which can be substituted by one or two Cl atoms or by one or two $C_1$- to $C_4$-alkyl groups or by $C_1$- to $C_4$-alkoxy or $C_1$- to $C_2$-carboalkoxy, or $C_7$- to $C_{14}$-phenylalkyl or a group of the formula (V)

$$\begin{matrix} R^7CH_3 & CH_3R^7 \\ & \\ R^8-N & \\ & \\ R^7CH_3 & CH_3 \end{matrix} \quad (V)$$

in which $R^7$=hydrogen or methyl and $R^8$=hydrogen, $C_1$- to $C_4$-alkyl which can be substituted by one OH group or, in the case of $C_3$-alkyl, can also be substituted by two OH groups, 2,3-epoxypropyl, allyl or benzyl, $R^3$ is identical with or different from $R^2$ and has the meanings indicated under $R^2$ and additionally represents $C_3$- to $C_{21}$-alkoxyalkyl or dimethylamino-$C_2$- to $C_5$-alkyl or diethylamino-$C_2$- to $C_5$-alkyl or, together with the N atom linking them, $R^2$ and $R^3$ represent a pyrrolidine ring or a piperidine, morpholine or hexamethyleneimine ring which is unsubstituted or substituted by up to four $C_1$- to $C_4$-alkyl groups, r, s and t represent identical or different integers from 2 to 6 and v represents an integer from 0 to 3; $R^4$ and $R^5$ are identical or different radicals having the meanings indicated under $R^2$ and T is a group of the formula (VI)

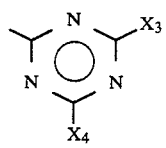 (VI)

in which X₃ and X₄ are identical or different radicals of the formulae (II), (III), or (IV) and $R^6$ represents one of the radicals listed under $R^2$, $R^1$ has the meaning of one of the radicals listed under $R^2$, $X_2$ represents one of the groups indicated under $X_1$, A is a group of the formula (VI) and, if $m=1$, Y is a $C_1$- to $C_{18}$- aliphatic acyl group which can be substituted by $-OH$ or $-Cl$, a $C_5$- to $C_{12}$-alicyclic acyl radical which can be substituted by $-OH$ or $C_1$- to $C_4$-alkyl, a $C_6$- or $C_{10}$-aromatic acyl or sulfonyl radical which can be substituted by $-OH$, $C_1$- to $C_4$-alkoxy, halogen or $-NH_2$, a $C_7$- to $C_{16}$-araliphatic acyl radical which can be substituted by $-OH$ and/or 1 or 2 $C_1$- to $C_4$-alkyl groups, or a $C_1$- to $C_{18}$-alkyl group, a $C_5$- to $C_{12}$-cycloalkyl group or a phenylcarbamoyl or napthylcarbamoyl group which can be substituted by halogen or by $C_1$- to $C_4$-alkyl, if $m=2$, Y represents a $C_2$- to $C_{18}$-aliphatic radical which can be substituted by up to two OH groups, a $C_3$- to $C_{12}$-alicyclic radical which can be substituted by $C_1$- to $C_4$-alkyl, a phenyl, naphthyl or $C_7$- to $C_{16}$-araliphatic diacyl radical which can be substituted by $-Cl$ or $C_1$- to $C_4$-alkyl, or a $C_2$- to $C_{12}$ aliphatic $\alpha,\omega$-dicarbamoyl group, or a phenylenedicarbamoyl group which can be substituted by $C_1$- to $C_4$-alkyl or chlorine, or a $C_7$- to $C_{18}$-araliphatic dicarbamoyl group which can be substituted by up to four $C_1$- to $C_4$-alkyl groups, if $m=3$, Y ' represents a $C_2$- to $C_5$-aliphatic or $C_6$-aromatic triacyl radical which can be substituted by up to two OH groups, or represents groups of the formulae

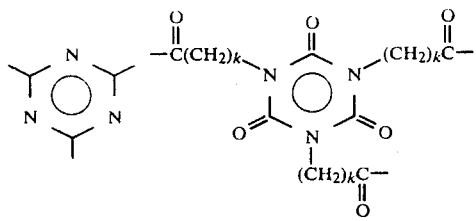

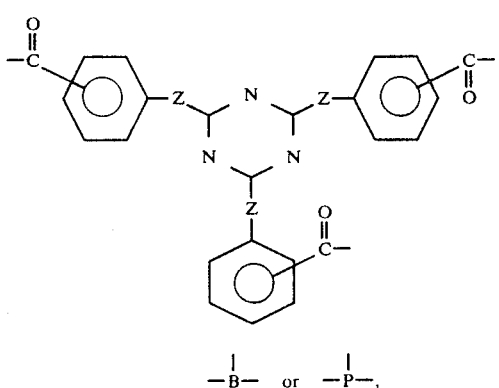

in which k is an integer from 1 to 6 and Z denotes $-O-$ or

if $m=4$, Y is a $C_4$- to $C_6$-aliphatic tetraacyl radical or a $C_6$- to $C_{10}$-aromatic tetraacyl radical or the group

if $m=5$ or 6, Y represents a $C_5$- to $C_8$-aliphatic or cycloaliphatic radical or, if $m>3$, represents an oligomeric acyl radical which is derived from acrylic acid or derivatives thereof, if $n>1$ and $m=1$, $X_2$ as a terminal group is halogen or one of the radicals

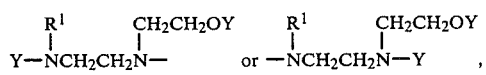

in which $R^1$ and Y have the meanings indicated above, A as a terminal group is H or Y, and at least one radical of the formula (V) must be present in formula (I), said process comprising:
(1) reacting in a process stage $A_1$, a cyanuric halide with a 0.95 to 1.05 molar quantity of a compound of the formula H-X₁ in which X₁ has the meaning indicated above, but is not halogen or phenyl, in the presence of an inert organic solvent and at $-5°$ to $40°$ C. to give a compound of the formula (VII)

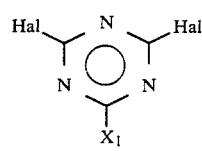 (VII)

(2) converting the latter in process stage $A_2$, at $10°$ to $70°$ C. by reaction with a 0.95 to 1.05 molar quantity of a compound of the formula H-X₂, in which X₂ has the meaning indicated above, but is not halogen or phenyl, into the derivative (VIII)

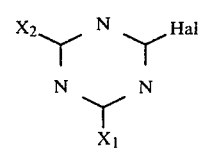 (VIII)

(3) and also, in process stage $A_3$, carrying out a condensation reaction at $50°$ to $200°$ C. with a 0.45 to 0.55 molar quantity of a compound of the formula (IX)

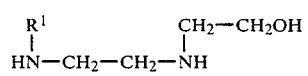 (IX)

in which $R^1$ has the meaning indicated above; thereby obtaining the products of the formula (Ic)

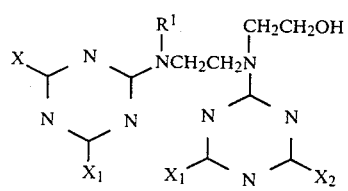 (Ic)
it being understood that process steps (2) and (3) need not be carried out in the order indicated; and converting these compounds (Ic) into derivatives by reaction with a quantity of an isocyanate, ester or acid chloride which is equivalent to the free OH groups in these compounds.
* * * * *

UNITED STATES PATENT AND TRADEMARK OFFICE
CERTIFICATE OF CORRECTION

PATENT NO. : 4,496,726

DATED : AUGUST 2, 1982

INVENTOR(S) : HARTMUT WIEZER ET AL

It is certified that error appears in the above-identified patent and that said Letters Patent is hereby corrected as shown below:

In column 1, line 62 the bracketed radical $\diagdown[(CH_2)_s \underset{T}{\overset{N}{|}}\, ]\!\!-$ of the side chain of Formula (III) should be taken $v$ times, so that it reads $-\!\!-\diagdown[(CH_2)_s \underset{T}{\overset{N}{|}}\, ]_v -\!\!-$ .

In column 5, the "$X_1$" substituent of the third structural formula down from the top of the column (the structural formula of "stage $A_3$") should read -- $X_2$ --.

UNITED STATES PATENT AND TRADEMARK OFFICE
CERTIFICATE OF CORRECTION

PATENT NO. : 4,496,726         Page 2 of 2
DATED      : AUGUST 2, 1982
INVENTOR(S): HARTMUT WIEZER ET AL It is certified that error appears in the above-identified patent and that said Letters Patent is hereby corrected as shown below:

In claims 1 and 3, those triazinyl structures shown as

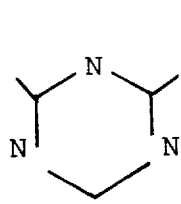     or     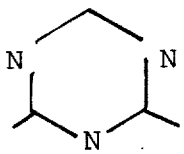

In column 17, line 15; column 19, line 55; column 20, line 53; and column 21, lines 2-4 should in all cases be aromatic rings and should therefore read:

-- 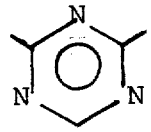     or     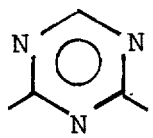 --

Signed and Sealed this

Nineteenth Day of November 1985

[SEAL]

Attest:

DONALD J. QUIGG

Attesting Officer    Commissioner of Patents and Trademarks